(12) United States Patent
Mask et al.

(10) Patent No.: US 7,518,479 B2
(45) Date of Patent: Apr. 14, 2009

(54) INLINE ELECTROMAGNETIC TOOL ACTUATOR

(76) Inventors: Thomas Mask, 3223 Golfstream Ct., Matthews, NC (US) 28105; Mark Evans, 136 Elm St., Mooresville, NC (US) 28115

( * ) Notice: Subject to any disclaimer, the term of this patent is extended or adjusted under 35 U.S.C. 154(b) by 0 days.

(21) Appl. No.: 11/513,603

(22) Filed: Aug. 31, 2006

(65) Prior Publication Data
US 2008/0055028 A1  Mar. 6, 2008

(51) Int. Cl.
*H01F 5/00* (2006.01)
*H01F 7/08* (2006.01)

(52) U.S. Cl. .................. 335/266; 335/212; 335/213; 335/219; 335/221; 335/222; 335/229; 335/230; 335/231; 335/232; 335/233; 335/234; 335/255; 335/256; 335/262; 335/299; 335/302

(58) Field of Classification Search ........... 335/212, 335/213, 219, 221–222, 229–234, 248–256, 335/262, 266, 299, 302
See application file for complete search history.

(56) References Cited

U.S. PATENT DOCUMENTS

| 3,762 | A | 10/1875 | Edison |
|---|---|---|---|
| 180,857 | A | 3/1876 | Edison |
| 196,747 | A | 4/1877 | Edison |
| 208,905 | A | 10/1878 | Griest |
| 5,009 | A | 12/1878 | Wilson |
| 464,801 | A | 12/1891 | O'Reilly |
| 3,035 | A | 2/1894 | MacDonald |
| 6,720 | A | 5/1897 | Glorget |
| 13,539 | A | 6/1899 | South |
| 768,413 | A | 4/1904 | Wagner |
| 215,629 | A | 7/1923 | Leresche |
| 1,724,812 | A | 8/1929 | Walters |
| 1,767,469 | A | 6/1930 | Metzner |

(Continued)

OTHER PUBLICATIONS

Ron Kurtus, "Alternating Current (AC) Transformers"; http://www.school-for-champions.com/science/actransormers.htm; pp. 1-7; Printed prior to Aug. 22, 2006.

(Continued)

*Primary Examiner*—Elvin G Enad
*Assistant Examiner*—Mohamad A Musleh
(74) *Attorney, Agent, or Firm*—Schwartz Law Firm, P.C.

(57) ABSTRACT

An inline electromagnetic tool actuator incorporates an actuator housing, an elongated armature, a tool assembly, spaced-apart return magnets, at least one drive magnet, and at least one magnet wire. The elongated armature is located inside the housing, and is adapted for reciprocating linear movement along a notional assembly axis. The tool assembly is operatively attached to the armature. The return magnets are located inside the housing, and are coaxially aligned with the armature. The return magnets have respective inward facing surfaces defining respective magnetic poles. The drive magnet is affixed to the armature, and is arranged between the return magnets. The drive magnet has opposing outward facing surfaces each of like polarity to adjacent inward facing surfaces of the return magnets. The magnet wire is coiled about the armature. When electrically charged with an alternating current, the wire creates an alternating magnetic field causing the drive magnet to bounce back and forth between repelling forces of the return magnets, whereby the armature and attached tool assembly reciprocate along the assembly axis relative to the housing.

20 Claims, 4 Drawing Sheets

U.S. PATENT DOCUMENTS

| | | | |
|---|---|---|---|
| 2,126,777 A | 8/1938 | Holt | |
| 2,840,076 A * | 6/1958 | Robbins | 604/46 |
| 3,039,467 A | 6/1962 | Stone | |
| 4,031,783 A | 6/1977 | Paul | |
| 4,159,659 A | 7/1979 | Nightingale | |
| 4,204,438 A | 5/1980 | Binaris | |
| 4,771,660 A | 9/1988 | Yacowitz | |
| 4,862,772 A | 9/1989 | Piperato | |
| 4,914,988 A | 4/1990 | Chang | |
| 5,054,339 A | 10/1991 | Yacowitz | |
| 5,279,570 A * | 1/1994 | Dombrowski et al. | 604/164.01 |
| 5,471,102 A * | 11/1995 | Becker et al. | 310/50 |
| 5,472,449 A * | 12/1995 | Chou | 606/186 |
| 5,586,473 A * | 12/1996 | Chou | 81/9.22 |
| D380,046 S | 6/1997 | Domanowski | |
| 5,661,446 A * | 8/1997 | Anderson et al. | 335/229 |
| 5,776,158 A | 7/1998 | Chou | |
| 5,959,374 A * | 9/1999 | Anderson et al. | 310/13 |
| 6,013,122 A | 1/2000 | Klitzman et al. | |
| 6,033,421 A * | 3/2000 | Theiss et al. | 606/186 |
| 6,039,014 A * | 3/2000 | Hoppie | 123/90.11 |
| 6,040,752 A * | 3/2000 | Fisher | 335/234 |
| D432,653 S | 10/2000 | Paolini | |
| 6,639,496 B1 * | 10/2003 | van Namen | 335/234 |
| 2003/0171767 A1 * | 9/2003 | Koplen | 606/185 |

OTHER PUBLICATIONS

"Tattoo Machine"; Tattoo Archive; http://www.tattooarchive.com/history/tattoo_machine.htm; pp. 1-4; Printed prior to Aug. 21, 2006.

"Sutherland Macdonald"; Tattoo Archive; http://www.tattooarchive.com/history/macdonald_sutherland.htm; pp. 1-3; printed prior to Aug. 21, 2006.

* cited by examiner

INLINE ELECTROMAGNETIC TOOL ACTUATOR

TECHNICAL FIELD AND BACKGROUND OF THE INVENTION

This invention relates generally to an inline electromagnetic tool actuator, and more specifically to an improved tattoo machine. The invention incorporates a unique inline construction which is compact and efficient, and comfortable in the hand. The tubular ergonomic design allows extended usage with less operator fatigue and discomfort.

SUMMARY OF THE INVENTION

Therefore, it is an object of the invention to provide an inline electromagnetic tool actuator which has particular application in the tattooing industry.

It is another object of the invention to provide an inline electromagnetic tool actuator which is highly efficient.

It is another object of the invention to provide an inline electromagnetic tool actuator which is compact and powerful.

It is another object of the invention to provide an inline electromagnetic tool actuator which is usable for an extended period with reduced operator fatigue and discomfort.

It is another object of the invention to provide an inline electromagnetic tool actuator which generates relatively little heat during operation.

It is another object of the invention to provide an inline electromagnetic tool Actuator which utilizes an alternating current supplied by a variable frequency, variable duty cycle, variable wave shape, external power supply.

It is another object of the invention to provide an inline electromagnetic tool actuator comprising a tattoo machine designed to allow precise control of needle depth, speed, and motive power.

These and other objects of the present invention are achieved in the preferred embodiments disclosed below by providing an inline electromagnetic tool actuator. The tool actuator comprises an actuator housing, an elongated armature, a tool assembly, spaced-apart return magnets, at least one drive magnet, and at least one magnet wire. The elongated armature is located inside the housing, and is adapted for reciprocating linear movement along a notional assembly axis. The tool assembly is operatively attached to the armature. The return magnets are located inside the housing and coaxially aligned with the armature. The return magnets have respective inward facing surfaces defining respective magnetic poles. The drive magnet is affixed to the armature and arranged between the return magnets. The drive magnet has opposing outward facing surfaces each of like polarity to adjacent inward facing surfaces of the return magnets. The magnet wire is coiled about the armature. When electrically charged with an alternating current, the wire creates an alternating magnetic field causing the drive magnet to bounce back and forth between repelling forces of the return magnets, whereby the armature and attached tool assembly reciprocate along the assembly axis relative to the housing.

Preferably, the return magnets comprise respective field magnets.

According to one preferred embodiment of the invention, the tool actuator comprises a plurality of spaced drive magnets affixed to the armature, and coaxially arranged such that like poles of adjacent drive magnets face one another.

According to another preferred embodiment of the invention, a stator tube surrounds the plurality of drive magnets.

According to yet another preferred embodiment of the invention, a plurality of spaced coil formers are coaxially arranged along a length of the stator tube.

According to yet another preferred embodiment of the invention, a plurality of wire coils are located in respective coil formers.

According to yet another preferred embodiment of the invention, adjacent ones of the wire coils are wrapped in opposite directions.

Preferably, the coils comprise a single magnet wire.

According to one preferred embodiment of the invention, first and second return wires are coiled about respective return magnets. When electrically charged, the return wires are adapted for adjusting the repelling forces of said return magnets.

According to another preferred embodiment of the invention, the tool assembly comprises an elongated needle and needle holder coaxially aligned with the assembly axis.

According to yet another preferred embodiment of the invention, a needle collet is affixed to a proximal end of the armature.

According to yet another preferred embodiment of the invention, a setscrew extends through the needle collet, and is adapted for selectively engaging the needle holder to releasably attach the needle holder to the armature.

According to yet another preferred embodiment of the invention, an ink tube surrounds the needle assembly and defines an ink well adapted for receiving and containing tattooing ink.

According to yet another preferred embodiment of the invention, a setscrew releasably attaches the ink tube to the housing.

Preferably, a cushioned finger grip is located on the ink tube.

According to one preferred embodiment of the invention, an AC power supply provides electric current to the magnet wire.

In another embodiment, the invention is a handheld tattooing machine comprising an inline electromagnetic needle actuator. The needle actuator comprises an actuator housing, an armature, a needle assembly, spaced-apart return magnets, at least one drive magnet, and at least one magnet wire. The armature is located inside the housing, and is adapted for reciprocating linear movement along a notional assembly axis. The needle assembly is operatively attached to the armature, and comprises a needle having a free end projecting from the housing. The return magnets are located inside the housing and are coaxially aligned with the armature. The return magnets have respective inward facing surfaces defining respective magnetic poles. The drive magnet is affixed to the armature and arranged between the return magnets. The drive magnet has opposing outward facing surfaces each of like polarity to adjacent inward facing surfaces of the return magnets. The magnet wire is coiled about the armature. When electrically charged with an alternating current, the wire creates an alternating magnetic field causing the drive magnet to bounce back and forth between repelling forces of the return magnets, whereby the armature and attached needle assembly reciprocate along the assembly axis relative to the housing.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

The present invention is described more fully hereinafterwith reference to the accompanying drawings, in which one or more preferred embodiments of the invention are shown. This invention may, however, be embodied in many different forms and should not be construed as limited to the embodiments set forth herein; rather, these embodiments are provided so that this disclosure will be operative, enabling, and complete. Like numbers refer to like elements throughout. As used herein, the article "a" is intended to include one or more items. Where only one item is intended, the term "one" or similar language is used. Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described.

Figure 1:
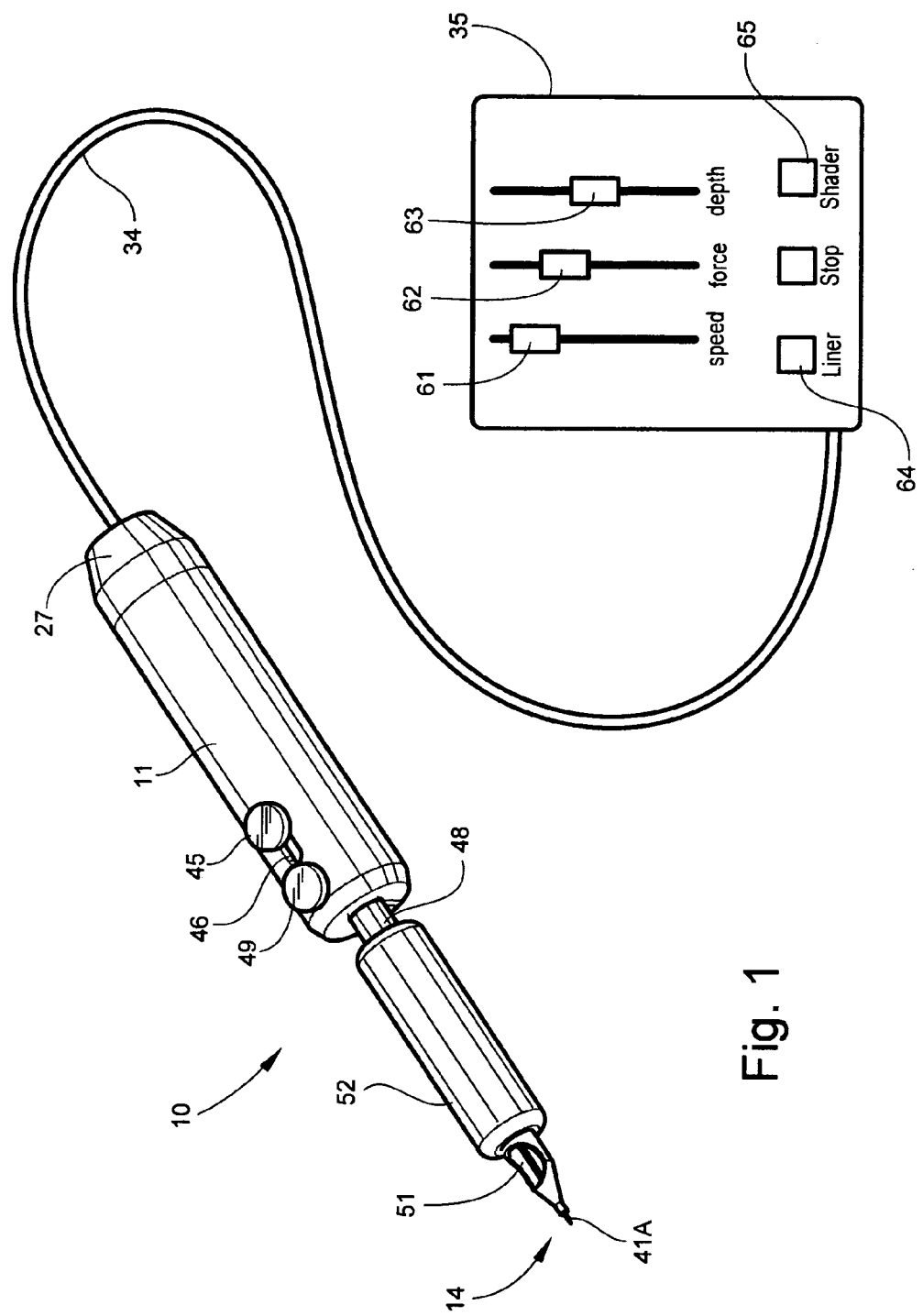
FIG. 1 is a perspective view of an inline electromagnetic tool actuator according to one preferred embodiment of the present invention.

Referring now specifically to the drawings, an inline electromagnetic tool actuator according to the present invention is illustrated in FIG. 1, and shown generally at reference numeral 10. According to one preferred application, the tool actuator 10 comprises a tattoo machine for applying pigment to the skin. The tool actuator 10 may also be used in a variety of other applications, including use in the medical industry for dermatological injections and in the jewelry industry for setting stones.

Figure 2:
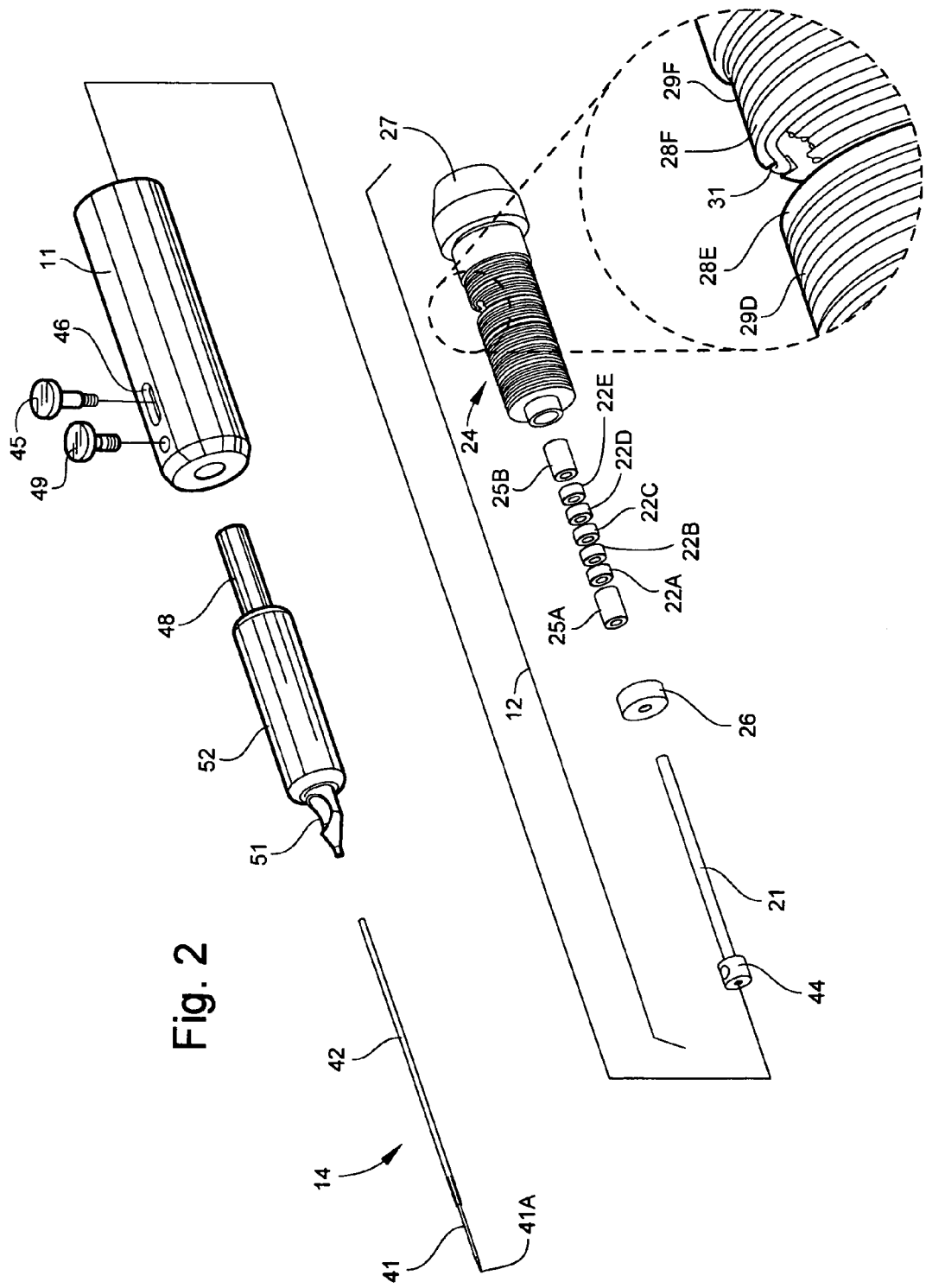
FIG. 2 is an exploded view of the tool actuator.

As best shown in FIG. 2, the tool actuator 10 incorporates a coaxial arrangement of parts including a tubular non-ferromagnetic actuator housing 11, an electromagnetic motor assembly 12 contained in the housing 11, and a needle assembly 14. The needle assembly 14 is operatively attached to the motor assembly 12, and designed for reciprocating linear movement relative to the housing 11.

The motor assembly 12 comprises an elongated non-ferromagnetic armature 21 located inside the housing 11, and including a series of spaced-apart coaxially aligned drive magnets 22A, 22B, 22C, 22D, and 22E (of like design)—each drive magnet 22A-22E having opposing annular faces defining respective magnetic poles. The drive magnets 22A-22E are affixed to the armature 21 and oriented such that like poles of adjacent magnets 22A-22E face one another (i.e., ns-sn-ns-sn-ns). Because the drive magnets 22A-22E are fixed relative to one another, the resulting force of repulsion between adjacent magnets acts not on the magnets themselves but instead on their respective magnetic fields. The magnetic fields extend outwardly from adjacent magnets 22A-22E at approximately 45 degrees to the like polar faces; the point of intersection of the magnetic fields forming a "virtual" magnetic pole. Preferably, the spacing between adjacent drive magnets 22A-22E is substantially equal to the width of a single drive magnet. While the motor assembly 12 shown incorporates five drive magnets 22A-22E, virtually any number of magnets may be employed (including only a single drive magnet) provided the orientation of polarity described herein is maintained.

The armature 21 and affixed drive magnets 22A-22E are substantially encased within an open-end, non-ferromagnetic stator tube 24. The stator tube 24 includes internal stationary return magnets 25A and 25B (of like design) located at its opposite ends, and having respective center openings sufficient to allow free sliding movement of the armature 21 therethrough relative to the stator tube 24. Each of the return magnets 25A, 25B has opposing annular faces defining respective magnetic poles coaxially aligned with outside magnetic poles of the end drive magnets 22A and 22E. The return magnets 25A, 25B are oriented such that the polarity of each inside face matches the polarity of the outside face of the adjacent end drive magnet 22A, 22E, thereby generating a repelling force between each return magnet 25A, 25B and the corresponding adjacent end drive magnet 22A, 22E. The repelling forces cooperate to center the armature 21 within the length of the stator tube 24 when the motor assembly 12 is idle. Preferably, the return magnets 25A, 25B are field (or permanent) magnets, or electromagnets. An end cap 26 serves to close the open end of the stator tube 24, and has a center opening allowing free reciprocating passage of the armature 21. An enlarged cap 27 is attached to the housing 11 at the opposite end of the stator tube 24 and defines a socket 27A adapted to receive an electrical connector (not shown) for supplying current to the motor assembly 12.

Figure 3:
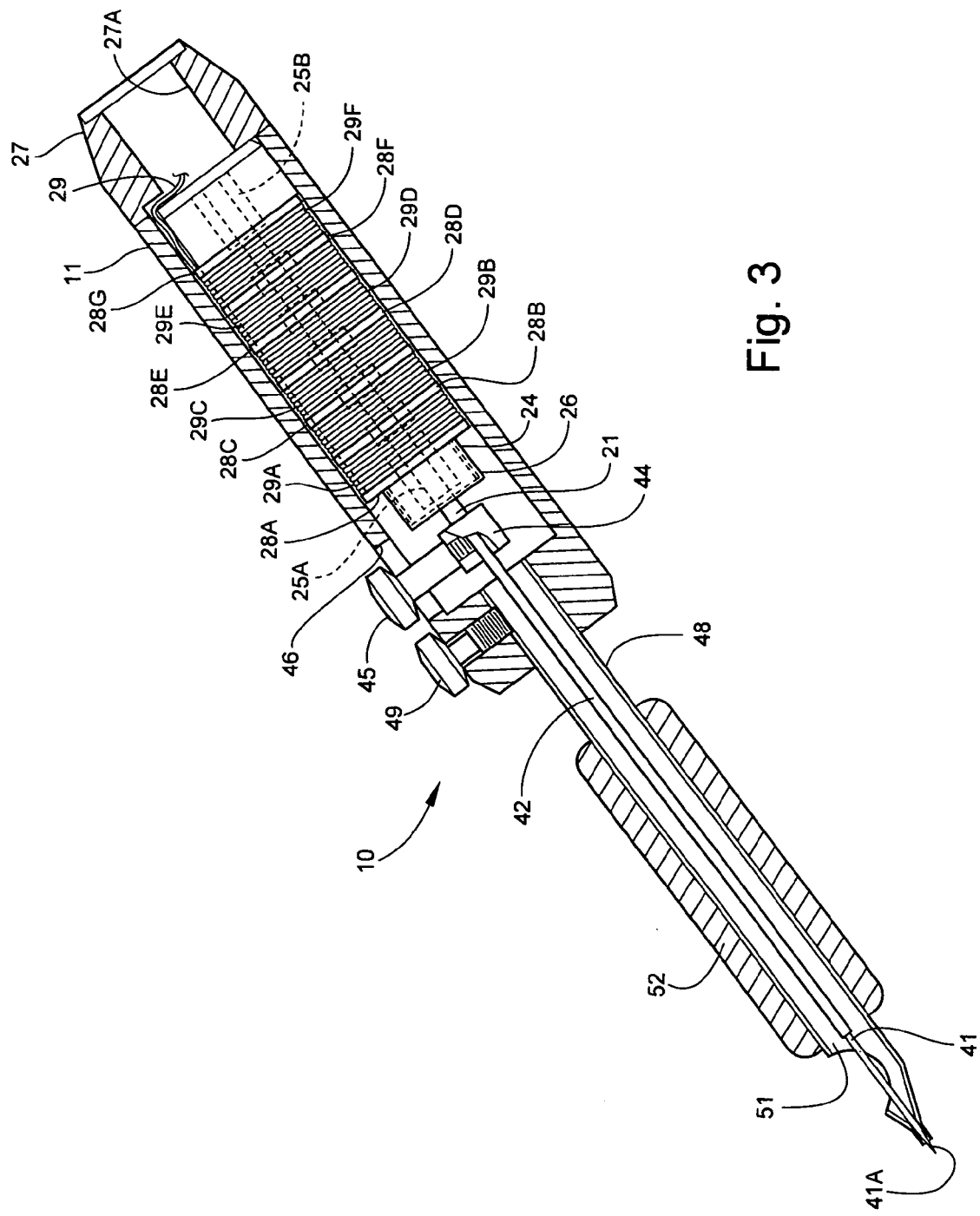
FIG. 3 is a cross-sectional view of the tool actuator.

As best shown in FIGS. 2 and 3, the stator tube 24 further comprises a number of axially-spaced, annular coil formers 28A, 28B, 28C, 28D, 28E, 28F, and 28G arranged along its exterior length. The coil formers 28A-28G segregate and divide respective wire coils 29A, 29B, 29C, 29D, 29E, and 29F. In the embodiment shown, the motor assembly 12 utilizes six coils 29A-29F which are radially off-set from respective drive magnets 22A-22E of the armature 21 such that with the armature 21 in its idle position, shown in FIG. 3, each drive magnet 22A-22E is substantially centered between two coils 29A-29F. For optimal operation, the number of the magnet wire coils 29A-29F is equal to the number of armature drive magnets 22A-22E plus one. Preferably, the spacing between adjacent coil formers 28A-28G is substantially equal to the spacing between adjacent drive magnets 22A-22E.

According to one embodiment, the wire coils 29A-29F are formed from a single magnet wire 29 which reverses its direction of wrap at adjacent formers 28A-28G, and which transitions between coils through small aligned notches 31 in the formers. When charged, the direction of current through the wire 29 reverses at each coil 29A-29F. Alternatively, the motor assembly 12 may incorporate multiple ends of wire connected in series and wrapped in opposite directions at adjacent coil formers 28A-28G. Since the armature drive magnets 22A-22E maintain a corresponding alternating orientation, when voltage is supplied to the wire 29 the armature 21 will move linearly until the repulsion force of the suspension magnets 25A, 25B is substantially equal to the electromotive force (emf) supplied by the wire 29. The repulsive linear arrangement provides for multiple "pushes" and "pulls" simultaneously thereby maximizing the efficiency of the magnetic coupling between the armature 21 and stator tube 24.

As best shown in FIG. 3, the terminal end of the magnet wire 29 exits the stator tube 24 through a passage to the socket 27A formed with the end cap 27. The magnet wire 29 is operatively connected to an electrical AC connector (not shown) which extends from electric wire 34 to a control box 35, shown in FIG. 1. The control box 35 serves to command actuation of the motor assembly 12, as discussed further below.

The needle assembly 14 comprises an exchangeable elongated needle 41 and needle holder 42 commonly employed in the art. The needle holder 42 is releasably attached to a non-ferromagnetic collet 44 located at a proximal end of the armature 21 using a setscrew 45, or other means. The setscrew 45 extends through a longitudinal slot 46 in the housing 11, and has an enlarged head which is conveniently rotated to clamp and release the needle holder 42 to and from the armature 21. The needle assembly 14 extends from the housing 11 through a sterile needle tube 48 coaxially aligned with the motor assembly 12. The needle tube 48 is releasably attached at its proximal end directly to the housing 11 using a second setscrew 49, or similar means. The free end of the needle tube 48 defines an ink well 51 for receiving and storing tattooing pigment. The tip 41A of the needle 41 projects from the needle tube 48, and operates to deliver the tattooing pigment to the skin. A cushioned finger grip 52 is preferably formed around a length of the needle tube 48.

Operation of the Tool Actuator 10

Figure 4A:
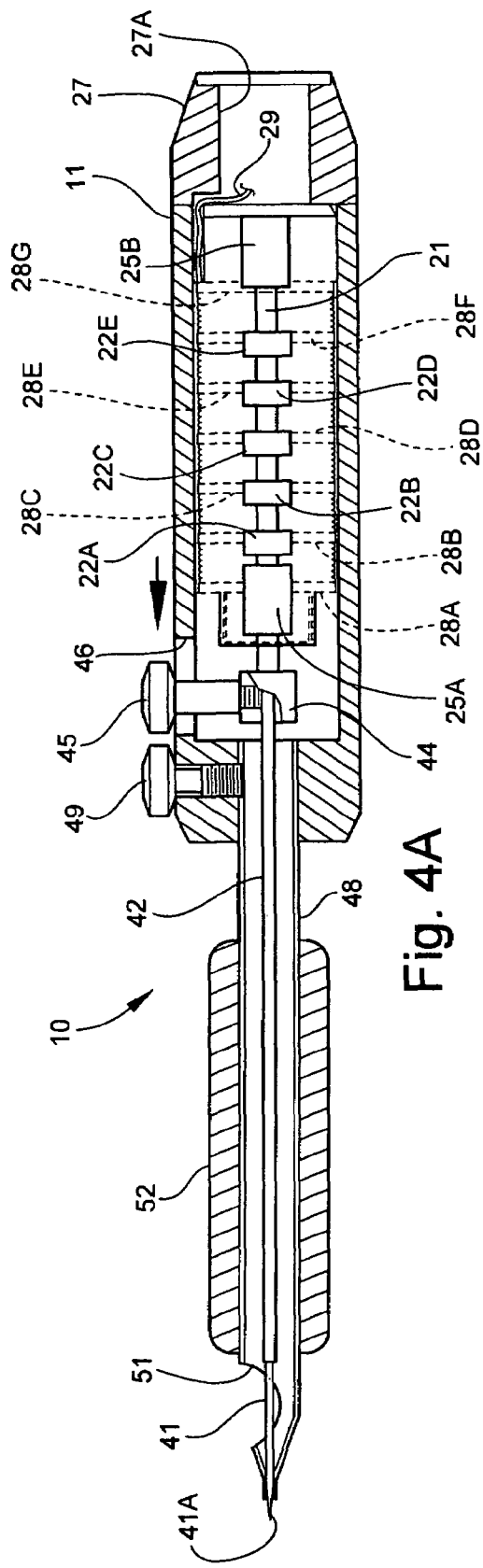
FIGS. 4A and 4B are further cross-sectional views illustrating sequential operation of the tool actuator.
Figure 4B:
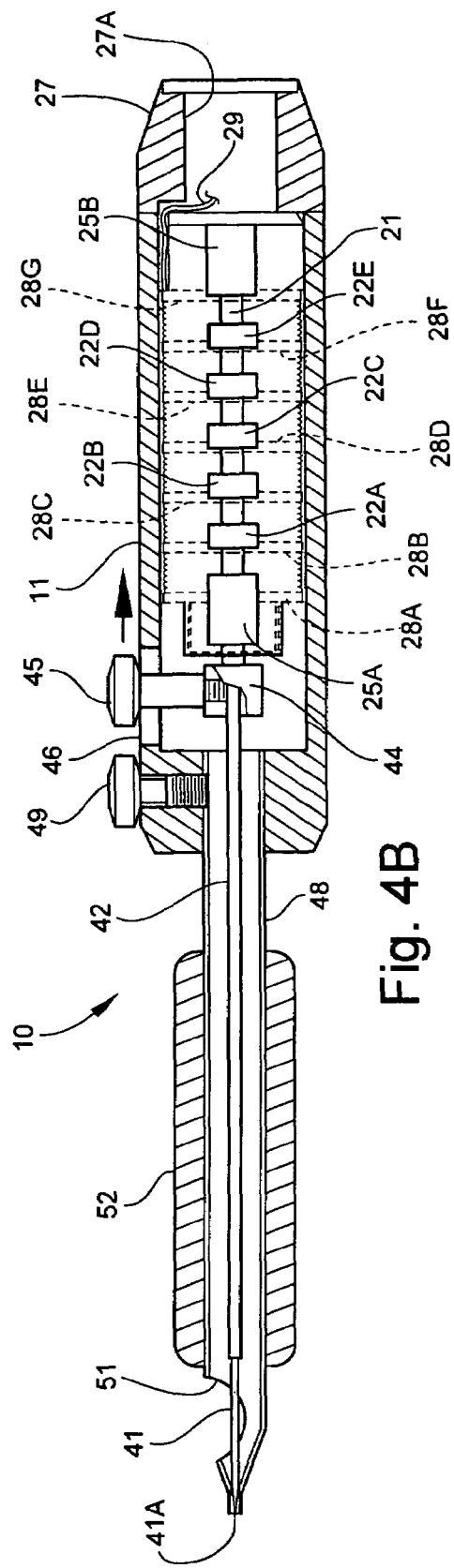

Referring to FIGS. 1, 4A, and 4B, the electromagnetic motor assembly 12 is activated by sending electric current from the control box 35 to the alternately coiled magnet wire 29 described above. The direction of the magnetic field is determined by the direction of the current and the direction of the wire coils 29A-29F around the stator tube 24. Thus, by changing the direction of the current, the north and south poles of the electromagnet will switch. In the present embodiment, in order to produce reciprocating linear movement of the armature 21 and needle assembly 14, the magnet wire 29 is supplied with an alternating voltage signal. While this can be accomplished through many means including mechanical points, digital timers, and optical sensors, the tool actuator 10 preferably utilizes an audio frequency oscillator circuit operating from 1 Hz to 200 Hz (typically about 110 Hz) combined with an audio amplifier circuit. The audio amplifier circuit serves to increase both voltage and current of the alternating signal to an optimally effective range. The amplified and adjusted signal is then electrically connected to the coiled magnet wire 29 of the motor assembly 12 to produce high-speed reciprocating linear movement of the armature 21 and attached needle assembly 14. FIGS. 4A and 4B demonstrate movement of the armature 21 and needle assembly 14 from a needle-extended position to a needle-retracted position, respectively. During operation the motor assembly 12, the return magnets 25A, 25B of the stator tube 24 act as frictionless springs which repel the end drive magnets 22A, 22E at each stroke of the armature 21. The slot 46 formed with the housing 11 allows the setscrew 45 to shift back and forth.

In a typical application, the armature 21 and needle assembly 14 travel about 2 mm with an operating voltage of 15V and a current of 0.3 A. Preferably, the circuits have user controls 61, 62, and 63 (indicated in FIG. 1) to adjust the frequency of oscillation, amplitude, duty cycle, and wave shape of the alternating signal. Further controls 64 and 65 may also be provided for a liner and shader. Additionally, voltage and current to the end coils 29A, 29F of the stator tube 24 may be separately controlled to adjust the repelling forces (or "spring tension") of the return magnets 25A, 25B.

An inline electromagnetic tool actuator is described above. No element, act, or instruction used in this description should be construed as critical or essential to the invention unless explicitly described as such. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims and their equivalents.

We claim:

1. An inline electromagnetic tool actuator, comprising
an actuator housing;
an elongated reciprocating armature located inside said housing, and adapted for reciprocating linear movement along a notional assembly axis;
a tool assembly operatively attached to said armature;
spaced-apart return permanent magnets located inside said housing and coaxially aligned with said armature, said return permanent magnets having respective inward facing surfaces defining respective magnetic poles, and at least one of said return magnets further defining a center opening through which said armature reciprocates;
at least one drive permanent magnet affixed to an outside of said armature and arranged between said return magnets, said drive magnet having opposing outward facing surfaces each of like polarity to adjacent inward facing surfaces of said return magnets; and
at least one magnet wire coiled about said armature, such that when electrically charged with an alternating current, said wire creates an alternating magnetic field causing said drive magnet to bounce back and forth between repelling forces of said return magnets, whereby said armature and attached tool assembly reciprocate relative to said housing.

2. A tool actuator according to claim 1, wherein said return magnets comprise respective field magnets.

3. A tool actuator according to claim 1, and comprising a plurality of spaced drive magnets affixed to said armature, and coaxially arranged such that like poles of adjacent drive magnets face one another.

4. A tool actuator according to claim 3, and comprising a stator tube surrounding said plurality of drive magnets.

5. A tool actuator according to claim 4, and comprising a plurality of spaced coil formers coaxially arranged along a length of said stator tube.

6. A tool actuator according to claim 5, and comprising a plurality of wire coils located in respective coil formers.

7. A tool actuator according to claim 6, wherein adjacent ones of said wire coils are wrapped in opposite directions.

8. A tool actuator according to claim 7, wherein said wire coils comprise a single magnet wire.

9. A tool actuator according to claim 1, and comprising first and second return wires coiled about respective return magnets, and when electrically charged adapted for adjusting the repelling forces of said return magnets.

10. A tool actuator according to claim 1, wherein said tool assembly comprises an elongated needle and needle holder coaxially aligned with said assembly axis.

11. A tool actuator according to claim 10, and comprising a needle collet affixed to a proximal end of said armature.

12. A tool actuator according to claim 11, and comprising a setscrew extending through said needle collet and adapted for selectively engaging said needle holder to releasably attach said needle holder to said armature.

13. A tool actuator according to claim 12, and comprising an ink tube surrounding said needle assembly and defining an ink well adapted for receiving and containing tattooing ink.

14. A tool actuator according to claim 13, and comprising a setscrew for releasably attaching said ink tube to said housing.

15. A tool actuator according to claim 14, and comprising a cushioned finger grip located on said ink tube.

16. A tool actuator according to claim 1, and comprising an AC power supply adapted for supplying electric current to said at least one magnet wire.

17. A handheld tattoo machine comprising an inline electromagnetic needle actuator, said needle actuator comprising:
- an actuator housing;
- a reciprocating armature located inside said housing, and adapted for reciprocating linear movement along a notional assembly axis;
- a needle assembly operatively attached to said armature, and comprising a needle having a free end projecting from said housing;
- spaced-apart return permanent magnets located inside said housing and coaxially aligned with said armature, said return magnets having respective inward facing surfaces defining respective magnetic poles and at least one of said return magnets further defining a center opening through which said armature reciprocates;
- at least one drive permanent magnet affixed to an outside of said armature and arranged between said return magnets, said drive magnet having opposing outward facing surfaces each of like polarity to adjacent inward facing surfaces of said return magnets; and
- at least one magnet wire coiled about said armature, such that when electrically charged with an alternating current, said wire creates an alternating magnetic field causing said drive magnet to bounce back and forth between repelling forces of said return magnets, whereby said armature and attached needle assembly reciprocate relative to said housing.

18. A tattooing machine according to claim 17, wherein said return magnets comprise respective field magnets.

19. A tattooing machine according to claim 18, and comprising first and second return wires coiled about respective return magnets, and when electrically charged adapted for adjusting the repelling forces of said return magnets.

20. A tattooing machine according to claim 17, and comprising a plurality of spaced drive magnets affixed to said armature, and coaxially arranged such that like poles of adjacent drive magnets face one another.

* * * * *